United States Patent
Gorokhovsky

(12) 
(10) Patent No.: US 6,722,883 B2
(45) Date of Patent: Apr. 20, 2004

(54) PROTECTIVE COATING FOR ABRASIVE DENTAL TOOLS AND BURS

(75) Inventor: Vladimir Gorokhovsky, Richmond Hill (CA)

(73) Assignee: G & H Technologies LLC, Florence, MT (US)

( * ) Notice: Subject to any disclaimer, the term of this patent is extended or adjusted under 35 U.S.C. 154(b) by 205 days.

(21) Appl. No.: 10/007,773

(22) Filed: Nov. 8, 2001

(65) Prior Publication Data

US 2004/0018468 A1 Jan. 29, 2004

Related U.S. Application Data

(60) Provisional application No. 60/247,039, filed on Nov. 13, 2000.

(51) Int. Cl.[7] .................................................. A61C 3/06
(52) U.S. Cl. ..................................................... 433/166
(58) Field of Search .................................. 433/166, 142, 433/165; 408/144, 145; 407/119; 51/295

(56) References Cited

U.S. PATENT DOCUMENTS

| | | | |
|---|---|---|---|
| 4,681,541 A | 7/1987 | Snaper | |
| 4,897,037 A | 1/1990 | Appleby | |
| 5,273,559 A | 12/1993 | Hammar | |
| 5,366,523 A * | 11/1994 | Rowenhorst et al. | ......... 51/293 |
| 5,376,444 A | 12/1994 | Grotepass | |
| 5,454,750 A * | 10/1995 | Cosmano et al. | ........... 451/526 |
| 5,823,775 A | 10/1998 | Aono | |
| 6,227,188 B1 * | 5/2001 | Tankala et al. | .......... 125/13.01 |
| 6,267,595 B1 * | 7/2001 | Gratz | ......................... 433/165 |

OTHER PUBLICATIONS

Borges, C.F.M. etal, "Dental diamond burs made with new technology" Journal of Prosthetic Dentistry, V 82, No. 1, p. 74–79. Orlando, Florida. USA.

* cited by examiner

*Primary Examiner*—Todd E. Manahan
(74) *Attorney, Agent, or Firm*—Saliwanchik, Lloyd & Saliwanchik

(57) ABSTRACT

A protective coating applied to abrasive layers of polycrystalline diamond located at the tip of abrasive dental tools is described. The protective coating is provided to protect the polycrystalline diamond layers in the course of storage, packaging, handling and sterilization. The protective coating is removable by abrasive forces when the cutting surfaces come into contact with porcelain and hard ceramic dental materials, teeth, bone or similar hard materials, and subsequently, the broken protective coating is rolled back and collected in the crevices and gaps of the polycrystalline diamond layer. The protective encapsulating coating can be made of a tough high melting point polymer layer, or a layer of a tough polymer also containing fine ceramic particles, or of a relatively soft, oxidation resistant metal or alloy.

10 Claims, 1 Drawing Sheet

PROTECTIVE COATING FOR ABRASIVE DENTAL TOOLS AND BURS

This application claims the benefit of U.S. Provisional Application No.: 60/247,039, filed Nov. 13, 2000.

FIELD OF INVENTION

This invention is related to abrasive dental tools and instruments, more particularly to dental tools such as dental burs, scrapers and similar scraping tools, which have polycrystalline diamond layers as abrasive surfaces.

BACKGROUND OF THE INVENTION

Abrasive dental tools and surgical instruments used in medically treating teeth of human beings, and in some instances animal teeth, carry abrasive particles on the tool surfaces applied for grinding teeth and bones in such treatments. The abrasive materials, most frequently polycrystalline diamond particles, are carried on a shank, which is supported securely in some type of a hand held drill or similar equipment, when in use. The shank is most commonly made of stainless steel or a similar tough, corrosion resistant, hard metal such as tungsten, or hard metal alloys. The shank is usually, but not necessarily, an elongated cylindrical body or rod. The abrasive layer of polycrystalline diamonds is usually applied as an adherent layer to an end portion of the shank only. The grinding action exerted by the abrasive particles is often enhanced by rotation of the shank at high speed.

The abrasive polycrystalline layer of polycrystalline diamond particles can be formed or deposited on the metallic shank in known ways, such as polycrystalline diamonds embedded in a nickel or nickel alloy matrix, or alternatively, embedded in a coating of polyurethane or similar hard polymer applied as a base coating onto the appropriate portion of the shank. The latter method of utilizing a polymer as a binding matrix for already formed diamond particles is described in U.S. Pat. No. 5,273,559, issued to Hammar et al. on Dec. 28, 1993. A dental bur shaped as a wedge bearing a thin cutting edge and having titanium or tungsten nitride or carbide formed by vapor deposition over the cutting edge is described in U.S. Pat. No. 4,681,541 which issued to A. A. Snaper on Jul. 21, 1987. Another method of obtaining an abrasive polycrystalline diamond layer is by chemical vapor deposition (CVD) from an ionized carbon bearing plasma. A polycrystalline diamond layer deposited directly over an end portion of the metal shank by high temperature vapor deposition is one of the preferred ways of obtaining polycrystalline diamond layers. However, one of the disadvantages of vapor deposited polycrystalline diamond layers is brittleness and low impact resistance.

Sterility and appropriate anti-bacterial conditions play a very important role in any intervention in the human or animate body, hence it is imperative that the abrasive surface bearing dental tool should be subjected to sterilization in the usual manner, before use. Hence the dental tool bearing the abrasive surface must be able to withstand the conditions of chemical and/or steam sterilization.

Another problem area which may arise with utilizing dental tools bearing polycrystalline diamond layers, is that the deposited layers occasionally have small crevices and similar discontinuities, which may subsequently give rise to dislodging and loss of small diamond crystals when in use as an abrasive tool or dental bur.

It is desirable to have a protective or encapsulating coating over the abrasive surfaces of polycrystalline diamonds, which can provide protection during packaging, transport, general handling and sterilization. It is noted that the present invention is directed to protection of the abrasive surface and bears little relation to how the abrasive surface has been obtained.

SUMMARY OF THE INVENTION

The object of the present invention is to provide a protective coating over the abrasive surface comprising polycrystalline diamonds during packaging, storing and sterilization, which coating is automatically removed from the cutting surfaces of the polycrystalline diamond layer when brought into contact with the teeth, bone, porcelain or other dental ceramic materials during a dental preparation or dental treatment procedure.

In one embodiment of the invention a tough polymer coating, which is capable of withstanding the conditions of sterilization, is applied to encapsulate the polycrystalline diamond layer directly after manufacturing, or after depositing the diamond layer over the appropriate surface of the shank or substrate. The protective capabilities of the polymer coating can be further increased by admixing hard ceramic materials of very small particles size in amounts up to 40 wt. % based on the weight of the polymer in the coating.

In another embodiment of the invention a malleable metallic layer, such as nickel, copper or an alloy of nickel or/and copper, or an alloy of copper-tin-titanium, which is softer than diamonds, is deposited by known means over the layer of polycrystalline diamond directly after manufacturing and/or subsequent to depositing the diamond layer over the appropriate surface of the shank or substrate.

DETAILED DESCRIPTION OF THE PRESENT INVENTION

Figure 1:
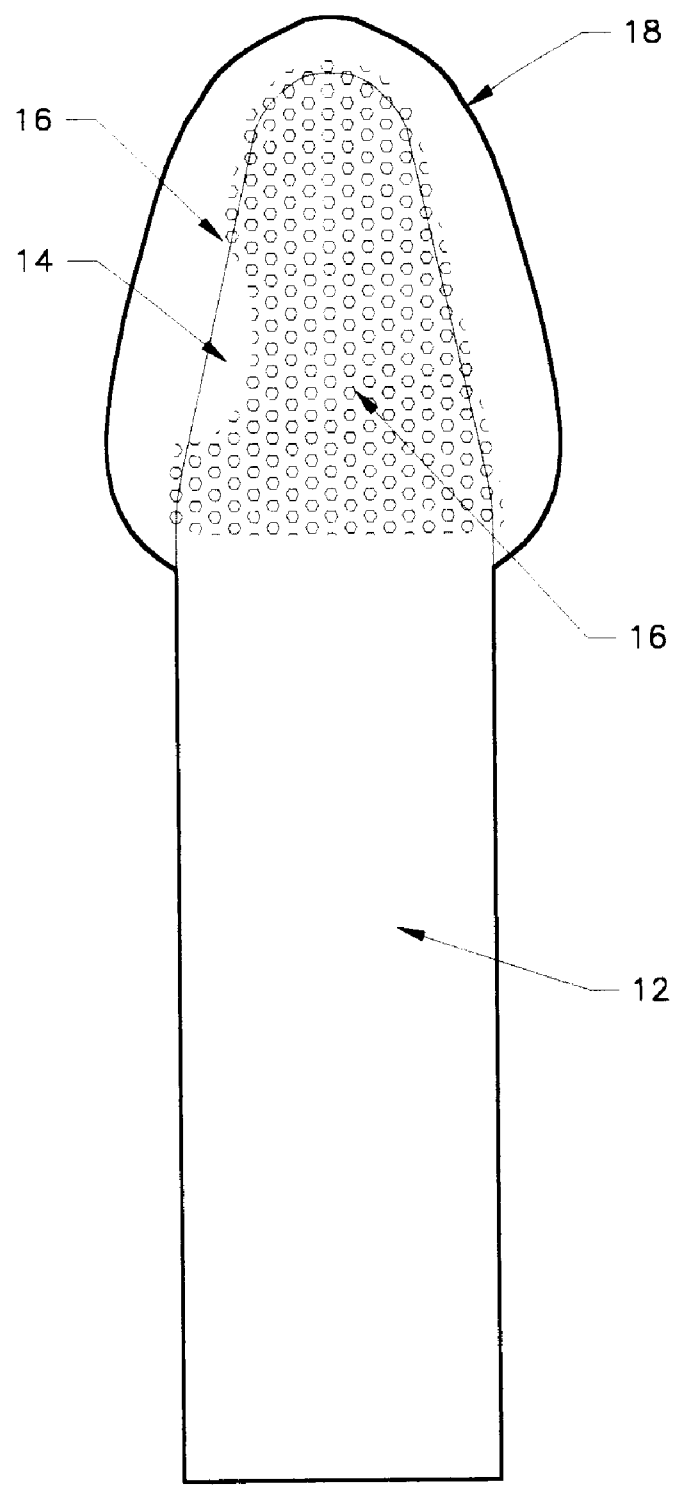
FIG. 1 is a schematic representation of the abrasive tip of a dental bur and the protective coating applied to encapsulate in accordance with the present invention.

Dental burs and similar dental tools used for drilling or scraping teeth usually comprise a stainless steel or similar hard metal or alloy, which is oxidation resistant, can be annealed by usual heat treatments if such is required, in the shape of an elongated cylinder or rod. The cylinder or rod may be coated with a polycrystalline diamond layer in its entirety or more frequently, only on a portion close to one end of the rod or shank. The surface to be coated may be shaped, or may be cylindrical or/and has a tapered finish. The shank surface which is to carry an adherent layer of polycrystalline diamonds, is often referred to as the substrate or substrate surface.

The polycrystalline diamond layer anchored to and carried on the substrate surface may be obtained by several known methods, such as embedding the polycrystalline diamonds in a nickel or nickel alloy matrix provided by known methods, or by first producing a tough, water and impact resistant polymer matrix and having polycrystalline diamond particles embedded therein. However, a more recently developed method for obtaining a polycrystalline diamond layer of even crystallite size and having layer thickness of 20 to 200 μm, is by high temperature plasma deposition from an ionized carbon containing gas atmosphere of appropriate composition.

The polycrystalline diamond layer obtained by chemical vapor deposition (CVD) is usually formed of diamond particles of even crystallite size, but such layer of particles may frequently be brittle and may have relatively low impact resistance. It is known that polycrystalline diamond coatings of layer thickness of 20 to 200 $\mu$m are very sensitive to impact during handling, storage, packaging, sterilization and similar process steps.

The dental tools, such as scrapers and dental burs, having polycrystalline diamonds as abrasive working surfaces, obtained as briefly described above, are usually packaged, transported to their destination, and sterilized by usual methods, require special and expensive measures to overcome the danger of being damaged, prior to and during use.

It has now been found that applying an encapsulating and protective coating of suitable material over the abrasive polycrystalline diamond surfaces diminishes brittleness, and increases the impact resistance of such dental tools. However, it is of importance that the encapsulating coating covering the entire cutting surfaces of the polycrystalline diamond layer, in addition to yielding protection, be removable from the cutting surfaces by the rotary or linear motion of the tool as soon as the abrasive dental tool comes in contact with the tooth, bone or ceramic dental material. In other words, the coating should be sufficiently soft that it is "rolled or stretched" back into the crevices between the crystalline cutting surfaces, on contact between the dental bur and the tooth, or the bone or the ceramic material of a crown. The receded or rolled back encapsulating coating material, which is softer than diamonds, will also act as elastic cushioning should any micro-crack appear between the polycrystalline diamonds, as well as accommodate any microscopic diamond particles that may have broken off during the abrasive treatment.

Another essential requirement of the protective coating is that it be resistant to conditions of normal and customary steam or chemical sterilization processes. In other words, the coating has to withstand the temperatures of sterilization, be unaffected by the pH of the sterilizing solution or any ultrasound treatment, and such like.

It is not unexpected that after one use of the polycrystalline diamond tool or dental bur, the cutting surfaces are too worn to be reused. However, should it be necessary, the remains of the coating moved away from the cutting surfaces are usually in good enough state to be subjected to repeated sterilization.

FIG. 1 shows schematically a dental bur, made of tungsten, stainless steel or a similar hard and corrosion resistant metal, having a cylindrical shank portion 12 and a tapered end portion 14. The tapered end portion 14, carries a polycrystalline diamond layer 16, anchored to the surface of the end portion. The encapsulating, protective coating 18, which is notably softer than the polycrystalline diamonds in layer 16, completely covers and coats the polycrystalline diamond layer and extends below the layer. The protective encapsulating coating has a thickness ranging between 10 between 200 $\mu$m, preferably between 15 and 120 $\mu$m.

In one embodiment of the invention the preferred encapsulating and coating material is a tough polymer such as polyurethane based compositions and derivatives, polyacrylates and derivatives, such as for example, bis-GMA resin, or any polymeric substance which satisfies the above discussed requirements. The protective capabilities of a polymer based encapsulating coating can be further increased by dispersing hard, abrasive ceramic particles of less than 5 $\mu$m size in the polymer solution before application to the diamond layer. The ceramic material used in such dispersion can be boron nitride, boron carbide, alumina, aluminum nitride, silicon carbide and chemical equivalents. The ceramic particles are admixed with the polymer solution in no greater than 40 wt. %, but preferably in the range of 15 to 30 wt. %, based on the solid content of the polymer solution. The abrasive ceramic particles as components of the polymer encapsulating coating provide increased erosion resistance during packaging, shipping, handling, and especially, during sterilization process steps.

In another embodiment the coating is a metal or alloy notably softer and malleable than diamonds, such as nickel or a nickel alloy, copper-tin alloy, copper-tin-titanium alloy, or an alloy of copper, tin and a transition metal further alloyed with titanium, and similar metallic compositions having the required properties. It is noted that when making up the titanium containing alloys, it is convenient and preferable that the titanium be added in the form of titanium hydride, which decomposes during firing and homogenization of the alloy, while advantageously reducing oxidation of the alloy prepared.

Examples are provided below to illustrate the working of each embodiment, but such examples are by no means considered restrictive.

EXAMPLE 1

Pre-treated tungsten rods of 2 mm diameter and 19 mm length for use as substrates for dental drills or burs, were subjected to a chemical vapor deposition process from an ionized carbon containing gas atmosphere in a known manner, to provide a polycrystalline diamond layer anchored to the surface of the substrate. The rods were held in an appropriate substrate holder and polycrystalline diamond coatings were deposited on one end portion of the rods, in a continuous layer of 80 $\mu$m average thickness and 2 mm lengths. The tungsten rods carrying adherent polycrystalline diamond layers at one end of the rod, were removed from the vapor depositing apparatus and the polycrystalline diamond bearing end portions were dipped in a commercially available polyurethane varnish, such as for example, marketed under the name of "Varathene Varnish", and the solvent allowed to evaporate. The obtained polyurethane varnish coating extended along the complete surface of polycrystalline diamond layer and even beyond the boundary of the diamond layer and the tungsten rod. The obtained encapsulating coating had average thickness of 30–40 $\mu$m.

The resulting dental burs encapsulated in a polyurethane coating were packaged, shipped and subsequently subjected to autoclave sterilization, and their performance in shaping and grinding dental crowns made of quartz and porcelain which have been previously cast and fired to meet certain dental requirements, was compared to dental burs obtained, packaged, shipped and sterilized in the same manner, but without having been encapsulated in a polyurethane polymer protective coating. It was found that the life-time of the dental burs having polyurethane encapsulation has been increased by 50% or by a factor of 1.5.

EXAMPLE 2

Dental burs were produced utilizing high purity tungsten rods of dimensions similar to the tungsten rods of Example 1, and applying the same ionized carbon deposition process to obtain vapor deposited polycrystalline diamond coatings anchored to the surface of the tips of the tungsten rods as in Example 1. The end portions of the tungsten rods bearing a continuous layer of polycrystalline diamonds had a commercially available light-curable, acrylic resin, such as "Bis-GMA" resin solution marketed by the Kerr Corporation, painted on its entire abrasive surface, providing an acrylic resin coating in an average depth of 15–30 μm, which was subsequently cured or polymerized by light treatment in a usual manner, to obtain a polyacrylic coating.

The cured polyacrylic resin encapsulated dental burs were packaged, transported and sterilized in the usual manner. The performance and life-span of cured and polymerized acrylic resin encapsulated dental burs were compared to conventional dental burs packaged, transported and sterilized in the same manner but without having been encapsulated in a polyacrylic polymer coating. It was found that the life-time of the dental burs having polyacrylic resin encapsulation has been increased by 66% or by a factor of 1.7.

EXAMPLE 3

Dental burs were produced utilizing high purity tungsten rods of dimensions similar to the tungsten rods of Example 1, and applying the same ionized carbon deposition process to obtain vapor deposited polycrystalline diamond coatings anchored to the surface of the tips of the tungsten rods as in Example 1. Commercially available polyurethane varnish solution was thoroughly mixed with fine boron nitride having particle size less than 1 μm, which was added in 20 wt. % based on the solid content of the polyurethane varnish solution. The polycrystalline diamond layer bearing tips of the dental burs were dipped in the ceramic particle containing polyurethane varnish to coat the diamond layers beyond its boundary with the tungsten rods, and the solvent was allowed to evaporate and the encapsulating coating to harden.

The resulting dental burs encapsulated in a polyurethane coating were packaged, shipped and subsequently subjected to autoclave sterilization, and their performance in shaping and grinding dental crowns made of quartz and porcelain which have been previously cast and fired to meet certain dental requirements, was compared to dental burs obtained, packaged, shipped and sterilized in the same manner, but without encapsulation in a polyurethane polymer protective coating. It was found that the life-time of the dental burs having polyurethane encapsulation has been increased by 100% or by a factor of 2.

EXAMPLE 4

Dental burs were obtained on stainless steel rods having dimensions as detailed in Example 1, and having polycrystalline diamond layers of 2 mm length and 100 μm depth at one end of the rods, obtained by applying a similar ionized carbon deposition process as in previous examples.

A composition of fine particles having average particle size of 5 μm, of tin, titanium hydride and copper were made up in a weight ratio of Cu:Sn:TiH=70:20:10. The fine particles were thoroughly mixed with a 10% solution of latex in benzene, resulting in a thick cream like paste. The paste was coated on the polycrystalline diamond layer of the burs, which were then heat-treated in a vacuum furnace at 800° C. for 15 minutes. The coated and fired dental burs, encapsulated in a copper-tin-titanium alloy were allowed to cool under vacuum, and subsequently packaged and shipped.

EXAMPLES 5–7

The diamond burs obtained as described in previous examples were provided with coatings made of alloys containing copper, tin, titanium hydride and one of iron, cobalt and chromium. The mixtures of fine metal particles were suspended in 10% benzene containing latex solution and this suspension was coated on the polycrystalline diamond layer bearing tips of the abrasive dental bur, and subsequently fired and cooled in vacuum as described in Example 4. The alloy composition of the coatings obtained, in weight ratios, were as follows:

Example 5: Cu:Sn:Fe:Ti=60:20:10:10;
Example 6: Cu:Sn:Co:Ti=60:20:10:10;
Example 7: Cu:Sn:Cr:TI=60:20:10:10.

It was found that the life-time of the above metal alloy encapsulated burs has been increased by well over 150%, or by a factor of at least 2.5, and in some instances threefold.

The dental tools having abrasive surfaces which are encapsulated in accordance with the present invention, can be packaged, transported and sterilized and thus be ready for use as when required, at a relatively low cost to the manufacturer.

Although the present invention has been described with reference to the preferred embodiments, it is to be understood that modifications and variations may be resorted to without departing from the spirit and scope of the invention, as those skilled in the art will readily understand. Such modifications and variations are considered to be within the purview and scope of the invention and the appended claims.

I claim:

1. A tool comprising:
   a continuous abrasive polycrystalline diamond layer deposited on a portion of the surface of the tool by chemical vapor deposition, the abrasive layer comprising at least one cutting surface; and
   a protective coating encapsulating the entire abrasive layer; wherein the protective coating is unaffected by the temperature, pressure and solution pH of sterilization process steps; and
   wherein the protective coating is removable by abrasive forces between the at least one cutting surface and another surface.

2. The tool of claim 1, wherein said another surface is a dental surface selected from the group consisting of: a tooth surface, a bone surface, and a ceramic dental crown previously cast and fired.

3. The tool of claim 1, wherein said protective coating is from about 10 μm to about 200 μm tick.

4. The tool of claim 1 wherein said protective coating comprises a polymer selected from the group consisting of: a polyurethane compound, a derivative of a polyurethane compound, a polyacrylic resin curable by light, and a derivative of an acrylic resin curable by light.

5. The tool of claim 4, wherein said protective coating further comprises less than about 40 percent by weight ceramic particles having a particle size of less than about 5 μm.

6. The tool of claim 4, wherein said protective coating is formed by a method selected from the group consisting of: dipping said abrasive layer covering said portion of said surface of said tool into an organic solution, and painting said coating over said abrasive layer.

7. The tool of claim 1, wherein said protective coating comprises a metal selected from the group consisting of: nickel and nickel alloys thereof, a copper-tin alloy, a copper-tin-titanium alloy, a copper-tin-iron-titanium alloy, copper-tin-cobalt-titanium alloy, and a copper-tin-chromium-titanium alloy.

8. The tool of claim 7, wherein said protective coating is formed by suspending fine metal particles in an organic solution, and firing said suspension at a high temperature to provide a continuous, solid metal bearing coating over said abrasive layer.

9. The tool of claim 1, wherein said tool is a dental tool.

10. The tool of claim 9, wherein said tool has at least one cutting edge.

* * * * *